US012226554B2

(12) United States Patent
Maben

(10) Patent No.: US 12,226,554 B2
(45) Date of Patent: Feb. 18, 2025

(54) SYSTEM AND METHOD FOR DISINFECTING AN INTERIOR OF AN AIRCRAFT

(71) Applicant: The Boeing Company, Chicago, IL (US)

(72) Inventor: Douglas D. Maben, Snohomish, WA (US)

(73) Assignee: The Boeing Company, Arlington, VA (US)

( * ) Notice: Subject to any disclaimer, the term of this patent is extended or adjusted under 35 U.S.C. 154(b) by 738 days.

(21) Appl. No.: 17/242,572

(22) Filed: Apr. 28, 2021

(65) Prior Publication Data

US 2021/0393840 A1     Dec. 23, 2021

Related U.S. Application Data

(60) Provisional application No. 63/041,466, filed on Jun. 19, 2020.

(51) Int. Cl.
*A61L 9/14* (2006.01)
*A61L 9/12* (2006.01)
*B64D 13/06* (2006.01)

(52) U.S. Cl.
CPC .............. *A61L 9/14* (2013.01); *A61L 9/122* (2013.01); *B64D 13/06* (2013.01); *A61L 2209/111* (2013.01); *A61L 2209/134* (2013.01); *A61L 2209/16* (2013.01)

(58) Field of Classification Search
CPC ... A61L 2/18; A61L 2/186; A61L 2/20; A61L 2/208; A61L 2/22; A61L 9/14; A61L 9/122; B64D 13/06; B64D 2013/0603
See application file for complete search history.

(56) References Cited

U.S. PATENT DOCUMENTS

| 7,901,618 | B2 * | 3/2011 | McVey | A61L 9/015 422/305 |
|---|---|---|---|---|
| 9,907,870 | B2 | 3/2018 | Boodaghians et al. | |
| 2005/0074359 | A1 | 4/2005 | Krieger et al. | |
| 2007/0158499 | A1 | 7/2007 | Whittingham | |
| 2009/0311138 | A1 | 12/2009 | Klaptchuk | |
| 2011/0091354 | A1 * | 4/2011 | Schwartz | F24F 8/24 422/111 |
| 2014/0271347 | A1 * | 9/2014 | Park | A61L 2/22 422/3 |
| 2017/0057643 | A1 * | 3/2017 | Frank | B64D 33/02 |

(Continued)

FOREIGN PATENT DOCUMENTS

| EP | 2 772 272 | 9/2014 |
|---|---|---|
| EP | 2 618 853 | 1/2016 |

(Continued)

OTHER PUBLICATIONS

European Patent Office, Extended European Search Report, App. No. 21180288.9 (Nov. 10, 2021).

(Continued)

*Primary Examiner* — Timothy C Cleveland
(74) *Attorney, Agent, or Firm* — Walters & Wasylyna LLC

(57) ABSTRACT

An aircraft includes an interior and an environmental system configured to circulate air through the interior. The aircraft also includes at least one disinfectant dispenser configured to dispense a disinfectant in the air circulated through the interior.

20 Claims, 7 Drawing Sheets

(56) References Cited

U.S. PATENT DOCUMENTS

2019/0201565 A1    7/2019   Shane et al.
2020/0046865 A1    2/2020   Shane et al.

FOREIGN PATENT DOCUMENTS

| | | |
|---|---|---|
| EP | 3354291 A1 | 8/2018 |
| EP | 2 777 716 | 12/2019 |
| JP | H 05-322218 | 12/1993 |
| JP | H 09-142397 | 6/1997 |
| JP | 2012-066755 | 4/2012 |
| WO | 2012011060 A1 | 1/2012 |
| WO | WO 2018/137003 | 8/2018 |

OTHER PUBLICATIONS

Translation of JP 2012-066755, Apr. 5, 2012.
Translation of JPH 05-322218, Dec. 7, 1993.
Translation of WO 2018/137003, Aug. 2, 2018..
Translation of JPH 09-142397, Jun. 3, 1997.
China National Intellectual Property Administration, Office Action, App. No. 202110663994.5 (Oct. 12, 2024).

\* cited by examiner

SYSTEM AND METHOD FOR DISINFECTING AN INTERIOR OF AN AIRCRAFT

CROSS-REFERENCE TO RELATED APPLICATIONS

This application is a non-provisional application of U.S. Patent Application No. 63/041,466, filed Jun. 19, 2020, and the entire disclosure of which is incorporated herein by reference.

FIELD

The present disclosure relates generally to aircraft and, more particularly, to systems and methods for disinfecting an interior of an aircraft.

BACKGROUND

At certain times, an interior of an aircraft must be disinfected. Disinfectants are typically applied by hand or are sprayed using manually operated sprayers. As such, manual disinfecting operations are laborious and time consuming. Additionally, manual disinfecting operations may expose a human applicator to potentially harmful chemicals. As such, personal protective equipment may be required to protect the human applicator. Furthermore, when applied to the interior of the aircraft, disinfectants may be drawn into functional systems by air circulation fans, which may damage components of the functional system. Accordingly, those skilled in the art continue with research and development efforts in the field of disinfecting operations of interiors of aircraft.

SUMMARY

Disclosed are examples of an aircraft, a disinfecting system for an aircraft, and a method of disinfecting an aircraft. The following is a non-exhaustive list of examples, which may or may not be claimed, of the subject matter according to the present disclosure.

In an example, the disclosed aircraft includes an interior and an environmental system configured to circulate air through the interior. The aircraft also includes at least one disinfectant dispenser configured to dispense a disinfectant in the air circulated through the interior.

In an example, the disclosed disinfecting system for an aircraft, including an interior and an environmental system, includes a disinfectant supply configured store a disinfectant and at least one disinfectant dispenser in fluid communication with the disinfectant supply and configured to dispense the disinfectant in air circulated through the interior by the environmental system.

In an example, the disclosed method of disinfecting an interior of an aircraft includes steps of: (1) circulating air through an interior of the aircraft; (2) dispensing a disinfectant in the air circulated through the interior; and (3) upon a predetermined condition, purging the disinfectant from the interior.

Other examples of the disclosed aircraft, disinfecting system and method will become apparent from the following detailed description, the accompanying drawings, and the appended claims.

DETAILED DESCRIPTION

Figure 1:
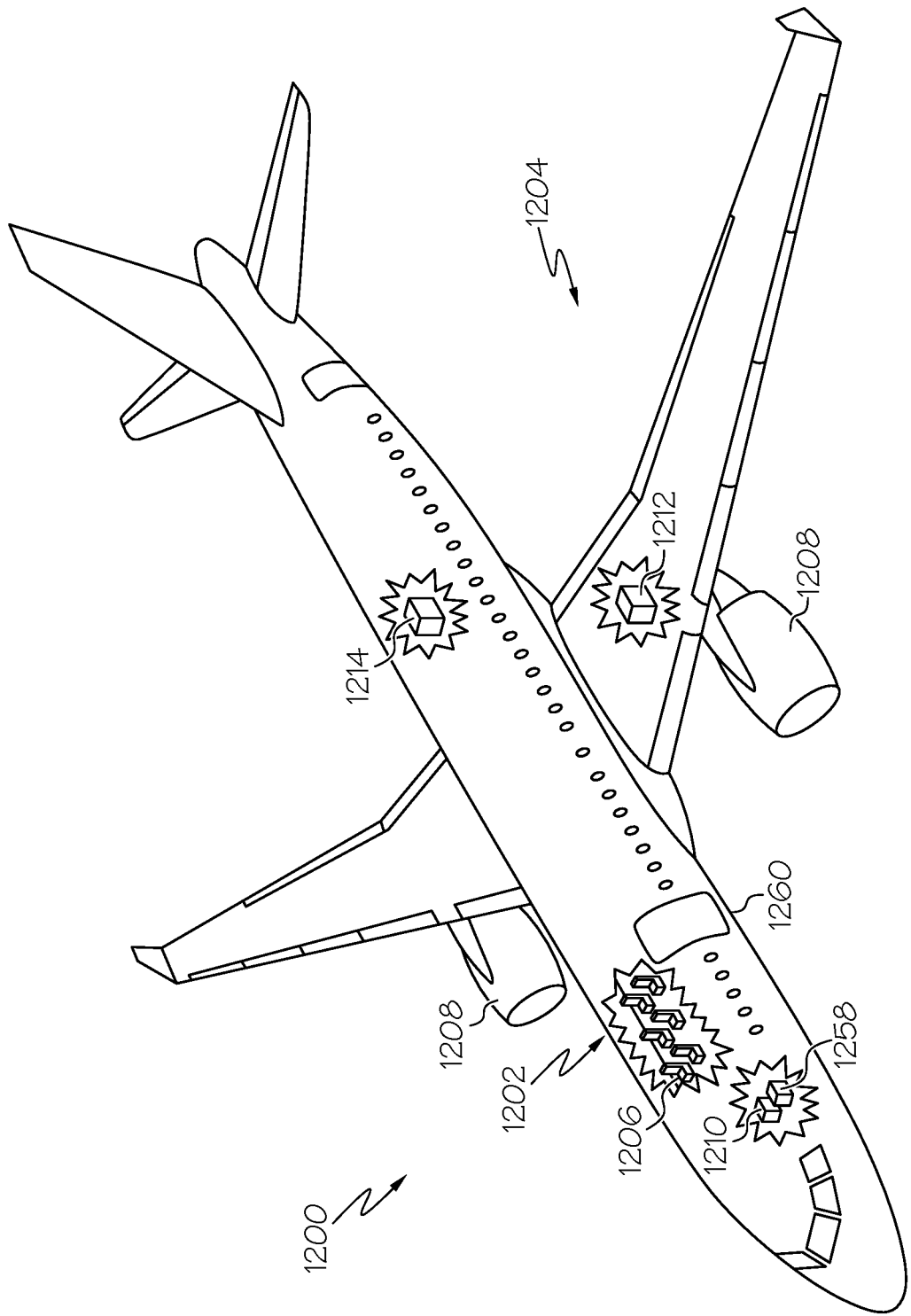
FIG. 1 is a schematic illustration of an example of an aircraft.

The following detailed description refers to the accompanying drawings, which illustrate specific examples described by the present disclosure. Other examples having different structures and operations do not depart from the scope of the present disclosure. Like reference numerals may refer to the same feature, element, or component in the different drawings.

Illustrative, non-exhaustive examples, which may be, but are not necessarily, claimed, of the subject matter according the present disclosure are provided below. Reference herein to "example" means that one or more feature, structure, element, component, characteristic, and/or operational step described in connection with the example is included in at least one aspect, embodiment, and/or implementation of the subject matter according to the present disclosure. Thus, the phrases "an example," "another example," "one or more examples," and similar language throughout the present disclosure may, but do not necessarily, refer to the same example. Further, the subject matter characterizing any one example may, but does not necessarily, include the subject matter characterizing any other example. Moreover, the subject matter characterizing any one example may be, but is not necessarily, combined with the subject matter characterizing any other example.

Figure 2:
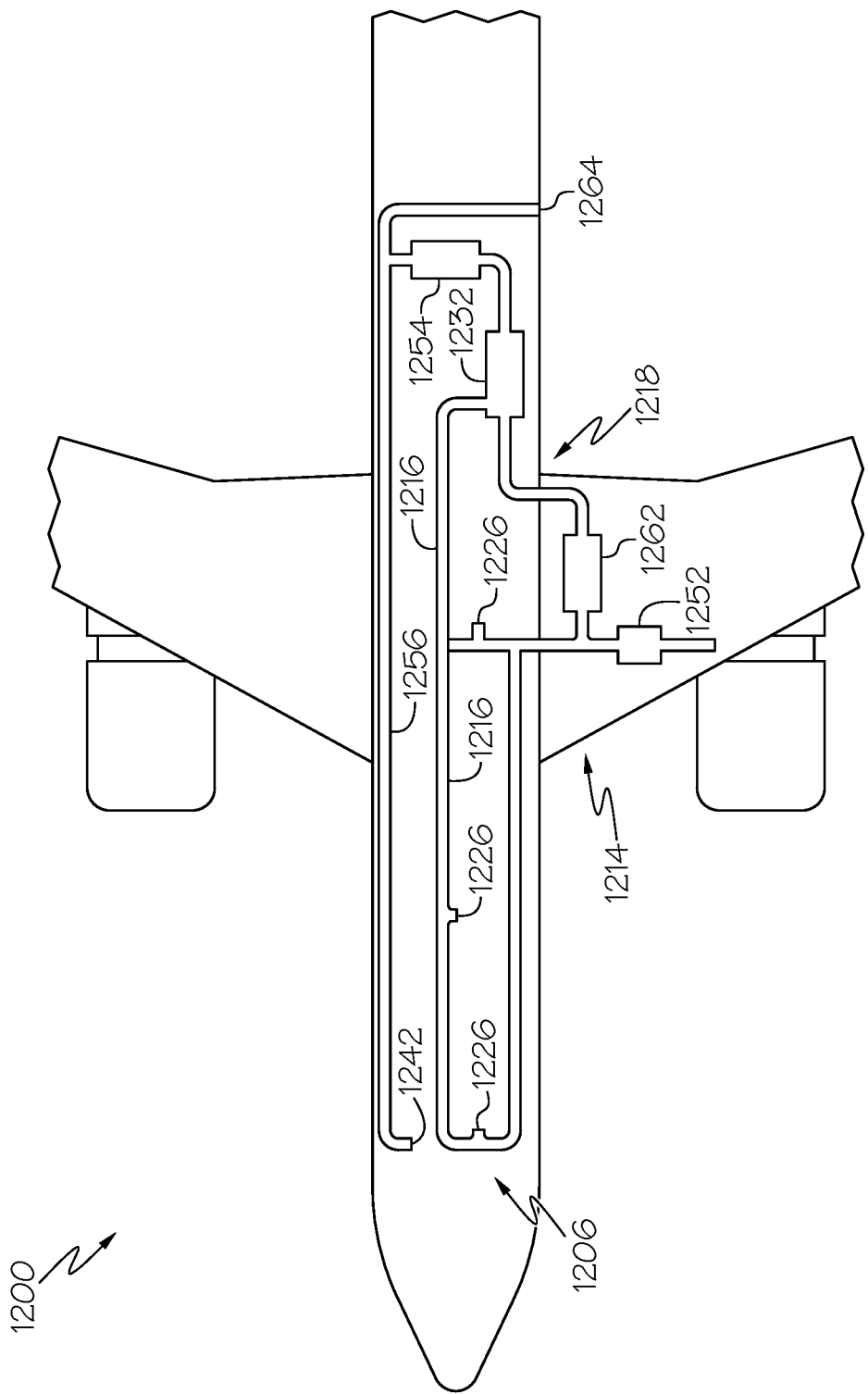
FIG. 2 is a schematic illustration of an example of an environmental control system of the aircraft.
Figure 3:
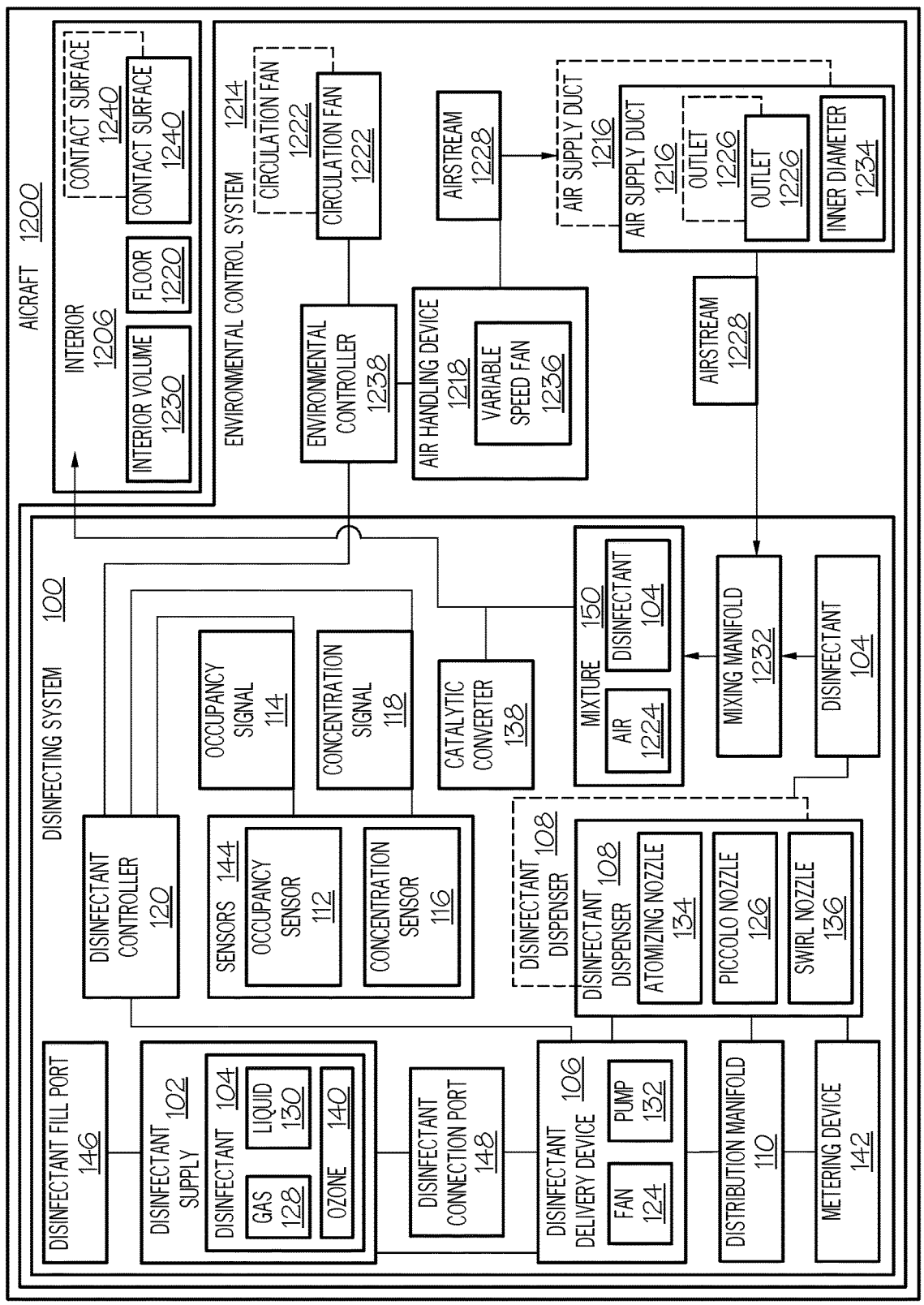
FIG. 3 is a schematic block diagram of an example of a disinfecting system for an interior of the aircraft.
Figure 4:
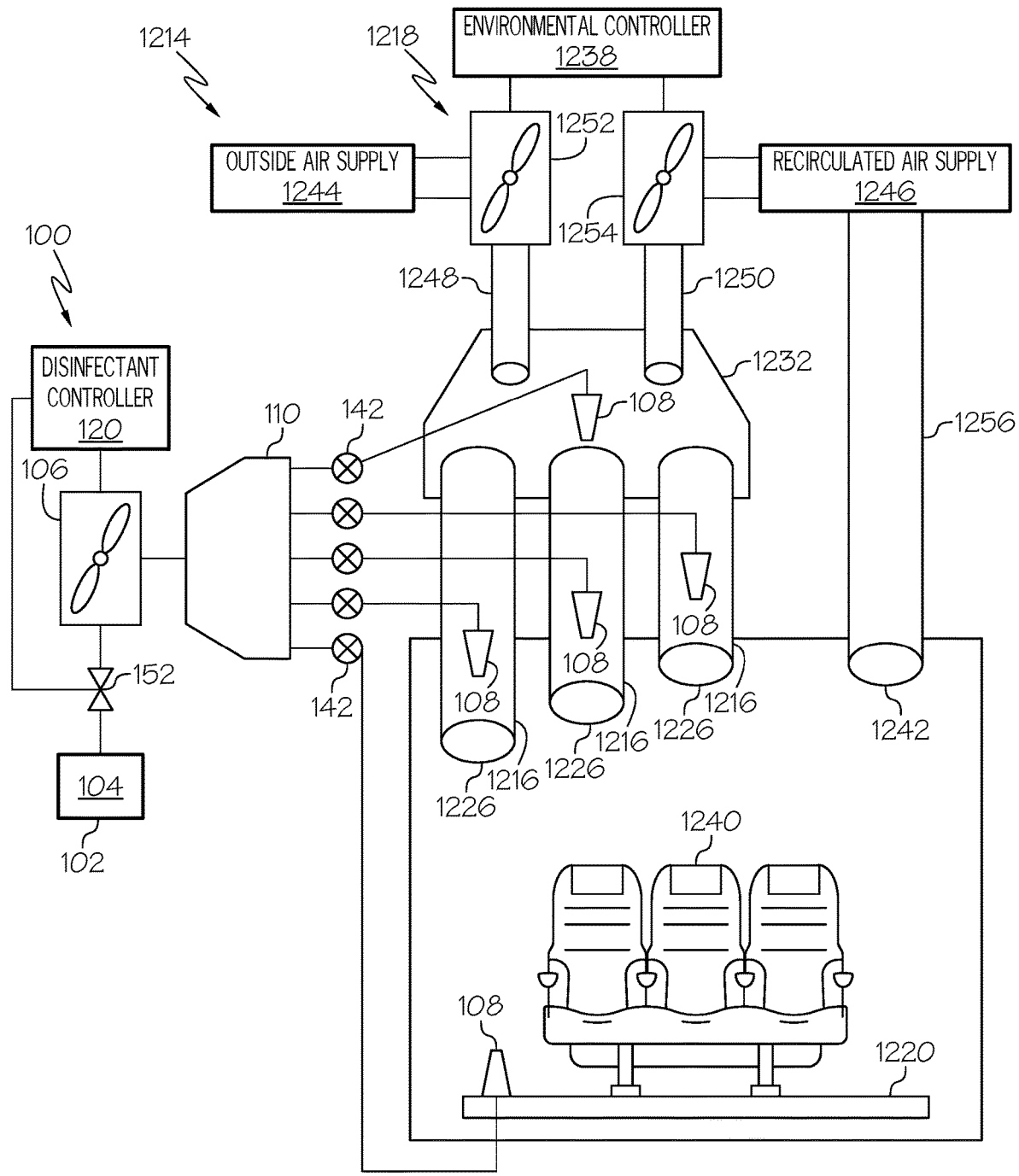
FIG. 4 is a schematic illustration of an example of the environmental control system and the disinfecting system.

Referring generally to FIGS. 1-4 and 6-8, by way of examples, the present disclosure is directed to an aircraft 1200 (e.g., as shown in FIG. 1) that includes a disinfecting system 100 (e.g., as shown in FIGS. 3 and 4) for rapidly and efficiently disinfecting an interior 1206 of the aircraft 1200.

Referring to FIG. 1, in one or more examples, the aircraft 1200 is a fixed-wing aircraft. However, in other examples, the aircraft 1200 may be any other type of aircraft. The aircraft 1200 includes a plurality of high-level systems 1204. Examples of the high-level systems 1204 include one or more of a propulsion system 1208, an electrical system 1210, a hydraulic system 1212, an environmental control ("environmental") system 1214, and a flight control system 1258. In other examples, the aircraft 1200 may include any number of other types of systems, such as a communications system, a guidance system, a weapons system, and the like.

The aircraft 1200 includes an airframe 1202. In one or more examples, the airframe 1202 forms a fuselage 1260, a pair of wings, and a tail. The fuselage 1260 generally defines an interior 1206 of the aircraft 1200, which may include a flight deck, a passenger compartment, a cargo compartment, and other compartments or service areas. The fuselage 1260 is the main body of the aircraft 1200 and includes any suitable central structure configured to hold a crew, one or more passengers, service equipment, and/or cargo.

In one or more examples, the propulsion system 1208 includes turbofan engines that are mounted to the wings of the aircraft 1200, for example, by pylons. In other examples, the engines may be mounted to the fuselage 1260 or other aircraft structures, such as the tail of the aircraft 1200. In various other examples, the propulsion system 1208 may include more or fewer engines and other types of engines (e.g., turboprop engines) may be used.

Referring to FIGS. 2-4, in one or more examples, the environmental system 1214 is configured to circulate air 1224 (e.g., as shown in FIG. 3) through the interior 1206 of the aircraft 1200. As used herein, the phrase "circulate air through the interior" and other similar phrases generally refer to a process that includes introducing air from outside of the interior 1206, moving the air through interior 1206, and discharging the air from the interior 1206. As used herein, the phrase "circulating air within the interior" and other similar phrases generally refer to moving air from one portion (e.g., compartment or area) of the aircraft 1200 to another portion (e.g., compartment or area) of the aircraft 1200 within the interior 1206 of the aircraft 1200.

Referring to FIGS. 2 and 3, in one or more examples of the aircraft 1200, the environmental system 1214 includes an air handling device 1218. The air handling device 1218 is configured to generate an airstream 1228 (e.g., as shown in FIG. 3) that circulates the air 1224 through the interior 1206 of the aircraft 1200. In one or more examples, the environmental system 1214 includes air supply ducts 1216. The air supply ducts 1216 are in fluid communication with the air handling device 1218. The air supply ducts 1216 are configured to direct the airstream 1228 within the interior 1206.

As illustrated in FIG. 2, in one or more examples, the air supply ducts 1216 are arranged within the interior 1206 of the aircraft 1200 such that the airstream 1228 (e.g., as shown in FIG. 3) is directed to at least the passenger compartment and a flight deck of the aircraft 1200. In other examples, the air supply ducts 1216 are arranged such that the airstream 1228 is directed to other areas of the interior 1206, such as a crew rest area, a galley, a lavatory, the cargo compartment, personal air outlets, and the like. As an example, a wide body commercial aircraft typically includes three to six cabin zones that form the passenger compartment. The air supply ducts 1216 are arranged so that the airstream 1228 is directed to each one of these cabin zones.

Referring to FIGS. 2-4, in one or more examples, the air supply ducts 1216 include a plurality of air supply outlets 1226. Each one of the air supply outlets 1226 is situated within the interior 1206 such that the airstream 1228 (e.g., as shown in FIG. 3) is directed to different areas within the interior 1206. In one or more examples, the environmental system 1214 also includes at least one return air inlet 1242 (e.g., as shown in FIGS. 2 and 4) that is situated within the interior 1206 such that the air within the interior 1206 is recirculated via at least one return air duct 1256 (e.g., as shown in FIGS. 2 and 4).

In one or more examples, the environmental system 1214 also includes an outflow valve 1264 (e.g., as shown in FIG. 2) that is in fluid communication with the interior 1206 of the aircraft 1200 and that is in fluid communication with outside of the aircraft 1200. The outflow valve 1264 is configured to maintain a predetermined pressure within the interior 1206. For example, as a quantity (e.g., volume) of air is introduced into the interior 1206 via the air supply outlets 1226 a corresponding quantity (e.g., volume) of air is discharged from the interior 1206 via the outflow valve 1264.

As illustrated in FIGS. 2 and 4, in one or more examples of the environmental system 1214, an outside air supply 1244 (e.g., as shown in FIG. 4) is drawn into the interior 1206. In an example, the outside air supply 1244 is drawn into the interior 1206 using an outside air supply fan 1252 that is in fluid communication with a conditioned air duct 1248 (e.g., as shown in FIG. 4). In one or more examples, the outside air supply fan 1252 is an example of, or forms a portion of, the air handling device 1218. In an example, bleed air passing through one or more of the engines of the aircraft 1200 is directed into the interior 1206. In another example, outside air is bled from different compressor stages within the engine (e.g., air is drawn in through compressors in at least one engine). In these examples, the outside air supply fan 1252 refers generally to, and may be referred to as, a compressor of the engine. In one or more examples, the outside air supply 1244 is conditioned (e.g., heated or cooled) using an air conditioning unit 1262 (e.g., as shown in FIG. 2).

In one or more examples of the environmental system 1214, a recirculated air supply 1246 (e.g., as shown in FIG. 4) is drawn from within the interior 1206, for example, using a recirculated air supply fan 1254 that is in fluid communication with the return air duct 1256 and with a recirculated air duct 1250 (e.g., as shown in FIG. 4). In one or more examples, the recirculated air supply fan 1254 is an example of, or forms a portion of, the air handling device 1218.

Referring to FIGS. 3 and 4, in one or more examples, the environmental system 1214 includes an environmental controller 1238. The environmental controller 1238 is in communication with the air handling device 1218, such as each one of the outside air supply fan 1252 and the recirculated air supply fan 1254. For example, the environmental controller 1238 is configured to selectively control each one of the outside air supply fan 1252 and the recirculated air supply fan 1254. As examples, at least one of the outside air supply fan 1252 and the recirculated air supply fan 1254 is selectively activated or selectively deactivated under direction from the environmental controller 1238. In one or more examples, at least one of the outside air supply fan 1252 and the recirculated air supply fan 1254 includes, or takes the form of, a variable speed fan 1236 (e.g., as shown in FIG. 3) such that the speed of at least one of the outside air supply fan 1252 and the recirculated air supply fan 1254 is selectively controlled under direction of the environmental controller 1238.

Referring to FIGS. 2 and 4, in one or more examples, the outside air supply 1244 and the recirculated air supply 1246 are directed to a mixing manifold 1232 where they are mixed to form the airstream 1228 (e.g., as shown in FIG. 3). In one or more examples, the air supply ducts 1216 are in fluid communication with the mixing manifold 1232 and direct the airstream 1228 from the mixing manifold 1232 to different areas of the interior 1206.

Referring to FIGS. 3 and 4, in one or more examples, the aircraft 1200 also includes at least one disinfectant dispenser 108. The at least one disinfectant dispenser 108 is configured to dispense a disinfectant 104 (e.g., as shown in FIG. 3) in the air 1224 (e.g., as shown in FIG. 3) circulated through the interior 1206.

Generally, the disinfectant 104 is any chemical agent designed to inactivate or destroy microorganisms, such as bacteria and viruses, on surfaces and in the air. Dispersing the disinfectant 104 into the air 1224 creates a disinfectant mixture 150 (e.g., as shown in FIG. 3) in a gaseous form or a gas mixed with liquid droplets of the disinfectant 104 that can cover a plurality of contact surfaces 1240 located within the interior 1206. As an example, filling the interior 1206 with the disinfectant mixture 150 facilitates rapid and efficient sanitization of a great number of contact surfaces 1240 and large contact surfaces 1240 as compared to other manual sanitizing operations. Additionally, filling the interior 1206 with the disinfectant mixture 150 facilitates sanitization of portions of the contact surfaces 1240 that may be missed during a manual sanitizing operation.

As illustrated in FIG. 4, in one or more examples, the at least one disinfectant dispenser 108 is located within the air supply duct 1216 (e.g., at least one of the air supply ducts 1216) of the environmental system 1214 to dispense the disinfectant 104 directly into the airstream 1228 within the air supply duct 1216.

Referring still to FIGS. 3 and 4, in one or more examples, the disinfecting system 100 and/or the aircraft 1200 includes at least one sensor 144 (e.g., as shown in FIG. 3). The at least one sensor 144 is configured to detect one or more conditions of the interior 1206 of the aircraft 1200. In one or more examples, the disinfecting system 100 and/or the aircraft 1200 also includes a disinfectant controller 120. The disinfectant controller 120 is configured to selectively control dispensation of the disinfectant 104 from the at least one disinfectant dispenser 108, for example, based on the one or more conditions detected by the at least one sensor 144.

In one or more examples, the disinfectant controller 120 is configured to monitor (e.g., periodically or continuously) the one or more conditions of the interior 1206, such as before introduction of the disinfectant 104 to the air 1224, while dispensing the disinfectant 104 in the air 1224, and after the disinfectant 104 is introduced to the air 1224.

In one or more examples, the disinfectant controller 120 is configured to selectively control one or more functional components of the environmental system 1214, such as the air handling device 1218, various variable speed fans 1236, various circulation fans 1222, and the like. As an example, the disinfectant controller 120 may be in communication with a plurality of functional components of the environmental system 1214 directly or indirectly via the environmental controller 1238. In an example, the disinfectant controller 120 is in communication with the environmental controller 1238 such that selective control of components of the environmental system 1214 are selectively controlled by the environmental controller 1238 under direction from the disinfectant controller 120.

In one or more examples of the disinfecting system 100 and/or the aircraft 1200, the one or more conditions includes at least one of occupancy of the interior 1206 and concentration of the disinfectant 104 in the air 1224. In other examples, the one or more conditions include any other measurable or determinable condition, such as internal pressure within the interior 1206, a circulation rate of the air 1224 through the interior 1206, and the like.

Referring still to FIGS. 3 and 4, in one or more examples of the disinfecting system 100 and/or the aircraft 1200, the at least one disinfectant dispenser 108 includes a plurality of disinfectant dispensers 108. In one or more examples, the disinfecting system 100 and/or the aircraft 1200 includes a disinfectant delivery device 106. The disinfectant delivery device 106 is in fluid communication with the plurality of disinfectant dispensers 108 (e.g., each one of the plurality of disinfectant dispensers 108). The disinfecting delivery device 106 is configured to deliver the disinfectant 104 to the plurality of disinfectant dispensers 108 (e.g., each one of the plurality of disinfectant dispensers 108).

In one or more examples, the disinfecting system 100 and/or the aircraft 1200 also includes a distribution manifold 110. The distribution manifold 110 is in fluid communication with the disinfectant delivery device 106 and is in fluid communication with the plurality of disinfectant dispensers 108. The distribution manifold 110 is configured to distribute the disinfectant 104 to each one of the plurality of disinfectant dispensers 108.

In one or more examples, the disinfecting system 100 and/or the aircraft 1200 includes at least one metering device 142. The metering device 142 is located between and is in fluid communication with the disinfectant delivery device 106 and with the plurality of disinfectant dispensers 108 (e.g., at least one disinfectant dispenser 108 or each one of the plurality of disinfectant dispensers 108). The metering device 142 is configured to selectively control a quantity of the disinfectant 104 delivered to the plurality of disinfectant dispensers 108 (e.g., at least one disinfectant dispenser 108 or each one of the plurality of disinfectant dispensers 108).

In one or more examples, the metering device 142 includes, or takes the form of, any mechanism suitable to regulate and selectively control a flow (e.g., mass flow or volumetric flow), a flow rate (e.g., mass flow rate or volumetric flow), or other parameter of a fluid. In one or more examples, the metering device 142 is in communication with the disinfectant controller 120 such that, under direction from the disinfectant controller 120, the metering device 142 controls the quantity of the disinfectant 104 delivered to the plurality of disinfectant dispensers 108 (e.g., at least one disinfectant dispenser 108 or each one of the plurality of disinfectant dispensers 108) from the disinfectant delivery device 106.

In one or more examples of the disinfecting system 100 and/or the aircraft 1200, the at least one metering device 142 includes a plurality of metering devices 142 (e.g., as shown in FIG. 4). Each one of the plurality of metering devices 142 is in fluid communication with the disinfectant delivery device 106 and with a corresponding one of the plurality of disinfectant dispenser 108. Each one of the plurality of metering devices 142 is configured to selectively control the quantity of the disinfectant 104 delivered to the corresponding one of the plurality of disinfectant dispensers 108.

In one or more examples, the disinfectant controller 120 is in communication with the disinfectant delivery device 106. The disinfectant controller 120 is configured to selectively initiate or selectively terminate delivery of the disinfectant 104 from the disinfectant delivery device 106 to the plurality of disinfectant dispensers 108 (e.g., at least one disinfectant dispenser 108 or each one of the plurality of disinfectant dispensers 108). Selective control of the disinfectant delivery device 106 facilitates selective control of dispersal of the disinfectant 104 from the plurality of disinfectant dispensers 108 (e.g., at least one disinfectant dispenser 108 or each one of the plurality of disinfectant dispensers 108).

In one or more examples, the plurality of disinfectant dispensers 108 (e.g., at least one disinfectant dispenser 108 or each one of the plurality of disinfectant dispensers 108) is selectively controllable by the disinfectant controller 120. As an example, the plurality of disinfectant dispensers 108 (e.g., at least one disinfectant dispenser 108 or each one of the plurality of disinfectant dispensers 108) is a "smart" dispenser that includes an actuatable valve (e.g., a solenoid) that is configured to selectively initiate, selectively terminate, or selectively control a flow of the disinfectant 104 through the disinfectant dispenser 108 under direction from the disinfectant controller 120

Referring to FIG. 3, in one or more examples, the disinfecting system 100 and/or the aircraft 1200 includes an occupancy sensor 112. The occupancy sensor 112 is in communication with the disinfectant controller 120. The occupancy sensor 112 is configured to generate an occupancy signal 114 that indicates whether the interior 1206 is occupied. The occupancy sensor 112 is an example of one of the plurality of sensors 144.

In one or more examples, the occupancy sensor 112 is suitably situated to detect the presence of a human in the interior 1206 of the aircraft 1200. In one or more examples, the disinfectant controller 120 is adapted (e.g., programmed) to determine whether the interior 1206 is occupied by a human based on the occupancy signal 114. In one or more examples, the occupancy sensor 112 includes, or takes the form of, at least one of an infrared (IR) sensor, a motion sensor, a proximity sensor, a thermal sensor, and the like. In one or more examples, the disinfecting system 100 and/or the aircraft 1200 includes a plurality of occupancy sensors 112.

In one or more examples, the disinfecting system 100 and/or the aircraft 1200 includes a concentration sensor 116. The concentration sensor 116 is in communication with the disinfectant controller 120. The concentration sensor 116 is configured to generate a concentration signal 118 that indicates a concentration of the disinfectant 104 in the air 1224 within the interior 1206 of the aircraft 1200. The concentration sensor 116 is an example of one of the plurality of sensors 144.

In one or more examples, the concentration sensor 116 is suitably situated to detect the concentration of the disinfectant 104 in the air 1224. In one or more examples, the disinfectant controller 120 is adapted (e.g., programmed) to determine the concentration of the disinfectant 104 in the air 1224 based on the concentration signal 118. In one or more examples, the concentration sensor 116 includes, or takes the form of, a gas sensor, an optical gas sensor, an electrochemical gas sensor, and the like. In one or more examples, the disinfecting system 100 and/or the aircraft 1200 includes a plurality of concentration sensors 116.

In one or more examples of the disinfecting system 100 and/or the aircraft 1200, the disinfectant controller 120 is configured to determine the concentration of the disinfectant 104 in the air 1224 within the interior 1206 based on an interior volume 1230 of the interior 1206 and a circulation rate of the air 1224 through the interior 1206. As used herein, the "circulation rate" refers to the rate at which a volume of gas (e.g., the air 1224 or the mixture 150 of the air 1224 and the disinfectant 104) enters and exits the interior 1206.

In one or more examples, the disinfectant controller 120 includes a computing device that includes a processor and memory, storing instructions that are executed by the processor. The disinfectant controller 120 is adapted (e.g., programmed) to determine (e.g., calculate) the concentration of the disinfectant 104 in the air 1224 (e.g., the disinfectant mixture 150) within the interior 1206 based on a plurality of known and/or controllable variables. In one or more examples, the interior volume 1230 of the interior 1206 and the circulation rate of the air 1224 through the interior 1206 are examples of the plurality of known and/or controllable variables. Additionally, the quantity (e.g., the flow or flow rate) of the disinfectant 104 dispersed into the airstream 1228 is also an example of a known and/or controllable variable, for example, based on the operating parameters of the disinfectant delivery device 106 and/or the at least one disinfectant dispenser 108. Further, a quantity (e.g., the flow or flow rate) of the air 1224 (e.g., the airstream 1228) that is directed into the interior 1206 is also an example of a known and/or controllable variable, for example, based on the operating parameters of the air handling device 1218.

Referring to FIGS. 2-4, in one or more examples of the aircraft 1200, the air handling device 1218 is configured to generate the airstream 1228 (e.g., as shown in FIG. 3) that circulates the air 1224 (e.g., as shown in FIG. 3) through the interior 1206. In one or more examples, the disinfectant controller 120 (e.g., as shown in FIGS. 3 and 4) is in communication with the air handling device 1218, such as via the environmental controller 1238 (e.g., as shown in FIGS. 3 and 4). The disinfectant controller 120 is configured to selectively activate or selectively deactivate the air handling device 1218, such as by providing instruction to the environmental controller 1238.

In one or more examples of the aircraft 1200, the air handling device 1218 includes at least one variable speed fan 1236 (e.g., as shown in FIG. 3). In one or more examples, the variable speed fan 1236 is at least one of the outside air supply fan 1252 (e.g., the engine compressor) (e.g., as shown in FIGS. 2 and 4) and the recirculated air supply fan 1254 (e.g., as shown in FIGS. 2 and 4).

In one or more examples, the air conditioning unit 1262 (e.g., as shown in FIG. 2) is configured to provide a variable flow of air 1224.

In one or more examples, the variable speed fan 1236 is an additional fan that is included in the environmental system 1214.

In one or more examples, the variable speed fan 1236 supplies variable flow (e.g., a variable airstream 1228) to the interior 1206 of the aircraft 1200. The disinfectant controller 120 is configured to, in response to at least one predetermined condition, increase a speed of the variable speed fan 1236 to increase the air flow (e.g., the airstream 1228) from the air handling device 1218, for example, to purge the disinfectant 104 from the interior 1206. Examples of the at least one predetermined condition includes, but are not limited to, achieving a predetermined (e.g., an effective) concentration of the disinfectant 104 in the air 1224, achieving a time period suitable for the disinfectant 104 to sanitize the contact surfaces 1240, achieving a predetermined internal pressure within the interior 1206, and the like. Generally, increasing the speed of the variable speed fan 1236 (e.g., at least one of the outside air supply fan 1252 and the recirculated air supply fan 1254) increases the flow and the circulation rate of the air 1224 through the interior 1206.

Referring still to FIGS. 2-4, in one or more examples of the aircraft 1200, the environmental system 1214 includes the plurality of air supply ducts 1216. The air supply ducts 1216 are in fluid communication with the air handling device 1218. The air supply ducts 1216 are configured to direct the airstream 1228 within the interior 1206. At least one disinfectant dispenser 108 is located within at least one of the air supply ducts 1216 to dispense the disinfectant 104 directly into the airstream 1228 within the air supply ducts 1216.

In one or more examples of the aircraft 1200, the air supply ducts 1216 include the plurality of air supply outlets 1226 located in the interior 1206. At least one disinfectant dispenser 108 is located upstream from the plurality of air supply outlets 1226 (e.g., as shown in FIG. 4). Situating at least one disinfectant dispenser 108 within the air supply ducts 1216 upstream from the air supply outlets 1226 facilitates proper mixing of the disinfectant 104 with the airstream 1228 within the air supply ducts 1216 before the airstream 1228 exits the air supply outlets 1226 and is introduced within the interior 1206.

In one or more examples of the aircraft 1200, the air supply ducts 1216 have an inner diameter 1234 (e.g., as shown in FIG. 3). In one or more examples, at least one disinfectant dispenser 108 is located upstream from any one of the plurality of air supply outlets 1226 by a distance of at least five times the inner diameter 1234. In one or more examples, at least one disinfectant dispenser 108 is located upstream from any one of the plurality of air supply outlets 1226 by a distance of less than five times the inner diameter 1234. The distance upstream of at least one disinfectant dispenser 108 from any one of the plurality of air supply outlets 1226 may depend on the form of the disinfectant 104. As an example, when the disinfectant 104 is in a gaseous form, the distance needed to ensure adequate mixing of the disinfectant 104 and the air 1224 may be at least five times the inner diameter 1234 of the air supply duct 1216. As another example, when the disinfectant 104 is in a liquid form, the distance needed to ensure adequate mixing of the disinfectant 104 and the air 1224 may be less than five times the inner diameter 1234 of the air supply duct 1216.

In one or more examples, the disinfecting system 100 and/or the aircraft 1200 includes the plurality of disinfectant dispensers 108. The disinfecting system 100 and/or the aircraft 1200 also includes the distribution manifold 110 in fluid communication with the disinfectant delivery device 106 and with the plurality of disinfectant dispensers 108. The distribution manifold 110 is configured to distribute the disinfectant 104 to each one of the plurality of disinfectant dispensers 108.

In one or more examples of the aircraft 1200, the air supply ducts 1216 include the plurality of air supply outlets 1226 located in the interior 1206. At least one of the plurality of disinfectant dispensers 108 corresponds to one of plurality of air supply outlets 1226 (e.g., as shown in FIG. 4). At least one of the plurality of disinfectant dispensers 108 is located within each one of the air supply ducts 1216 upstream from a corresponding one of the plurality of air supply outlets 1226 to dispense the disinfectant 104 directly into the airstream 1228 within each one of the air supply ducts 1216.

Referring still to FIGS. 2-4, in one or more examples, the disinfecting system 100 and/or the aircraft 1200 includes the mixing manifold 1232. The mixing manifold 1232 is located between and is in fluid communication with the air handling device 1218 and the air supply ducts 1216. As illustrated in FIG. 4, in one or more examples, at least one disinfectant dispenser 108 is located within the mixing manifold 1232 to dispense the disinfectant 104 directly into the airstream 1228 within the mixing manifold 1232.

Situating at least one disinfectant dispenser 108 within the mixing manifold 1232 reduces the number of disinfectant dispensers 108 required by creating the disinfectant mixture 150 (e.g., as shown in FIG. 3) within the mixing manifold 1232 and distributing the disinfectant mixture 150 to the plurality of air supply ducts 1216.

In one or more examples, at least one of the plurality of disinfectant dispensers 108 is located within the mixing manifold 1232 and at least one of the plurality of disinfectant dispensers 108 is located within one or more of the air supply ducts 1216.

Referring to FIGS. 3 and 4, in one or more examples of the aircraft 1200, the interior 1206 includes a floor 1220. In one or more examples, at least one disinfectant dispenser 108 (e.g., at least one of the plurality of disinfectant dispensers 108) is coupled to the floor 1220 to dispense the disinfectant 104 directly into the air 1224 within the interior 1206 (e.g., as shown in FIG. 4). Locating at least one disinfectant dispenser 108 on the floor 1220 within the interior 1206 enables the disinfectant 104 to mix with the air 1224 as the air 1224 is circulated within the interior 1206.

As illustrated in FIG. 4, in one or more examples, at least one of the plurality of disinfectant dispensers 108 is located within of the mixing manifold 1232, at least one of the plurality of disinfectant dispensers 108 is located within at least one of or each one of the air supply ducts 1216, and at least one of the plurality of disinfectant dispensers 108 is located on the floor 1220.

Referring to FIG. 3, in one or more examples, the aircraft 1200 includes a plurality of circulation fans 1222 located within the interior 1206. The circulation fans 1222 are configured to circulate the air 1224 within the interior 1206. In an example, the circulation fans 1222 are configured to move air 1224 between different portions (e.g., compartments, areas, cabin zones, etc.) of the interior 1206 that include at least one of the air supply outlets 1226 (e.g., as shown in FIGS. 2 and 4). In another example, the circulation fans 1222 are configured to move air 1224 from a portion of the interior 1206 that includes at least one of the air supply outlets 1226 to any other portion of the interior 1206 that does not include at least one of the air supply outlets 1226. As an example, electronic components of the aircraft 1200 (e.g., components of the electrical system 1210, components of the flight control system 1258, components of the communications system, and the like) may be located in portions of the interior 1206 that do not have one of the air supply outlets 1226. As such, these portions of the interior 1206 may receive air 1224, such as to cool the electronic components, via the circulation fans 1222.

In one or more examples of the disinfecting system 100 and/or the aircraft 1200, the disinfectant controller 120 is in communication with the plurality of circulation fans 1222. As an example, the disinfectant controller 120 may be in communication with the plurality of circulation fans 1222 directly or indirectly via the environmental controller 1238. The disinfectant controller 120 is configured to selectively activate or selectively deactivate each one of the plurality of circulation fans 1222. In an example, the disinfectant controller 120 may deactivate one or more of the circulation fans 1222 while the disinfectant 104 is within the interior 1206 to prevent the disinfectant 104 from encountering (e.g., coming into contact with) undesirable surfaces, equipment, filters, and the like.

In one or more examples, the disinfecting system 100 and/or the aircraft 1200 includes a disinfectant supply 102. The disinfectant supply 102 is configured to store the disinfectant 104. The disinfectant supply 102 is in fluid communication with the disinfectant delivery device 106. The disinfectant supply 102 includes, or takes the form of, any container (e.g., reservoir or tank) suitable to hold a volume of the disinfectant 104, depending on the form of the disinfectant 104.

In one or more examples of the disinfecting system 100 and/or the aircraft 1200, the disinfectant supply 102 is located within the interior 1206. In these examples, the disinfectant supply 102 is refillable.

In one or more examples, the disinfecting system 100 and/or the aircraft 1200 includes a disinfectant connection port 148. The disinfectant connection port 148 is in fluid communication with the disinfectant delivery device 106. In one or more examples, the disinfectant connection port 148 is located outside of the interior 1206 and the disinfectant supply 102 is located outside of the interior 1206. The disinfectant supply 102 is configured to be fluidly coupled with the disinfectant connection port 148. In these examples, when located outside of the aircraft 1200, the disinfectant supply 102 is portable and is releasably connected to the disinfectant delivery device 106, via the disinfectant connection port 148, prior to initiation of the disinfecting operation.

In one or more examples, the disinfecting system 100 and/or the aircraft 1200 includes a disinfectant fill port 146. The disinfectant fill port 146 is in fluid communication with the disinfectant supply 102 and is configured to enable an amount of the disinfectant 104 to be supplied to (e.g., within) the disinfectant supply 102.

Referring still to FIG. 3, in one or more examples of the disinfecting system 100 and/or the aircraft 1200, the disinfectant 104 is a gas 128. The disinfectant delivery device 106 includes a fan 124. In one or more examples, the disinfectant 104 includes any suitable gaseous disinfectant material, such as at least one of a chemical-based gas, ionized air gas, ozone, and the like. In one or more examples, the fan 124 includes any suitable gas moving device.

Figure 8:
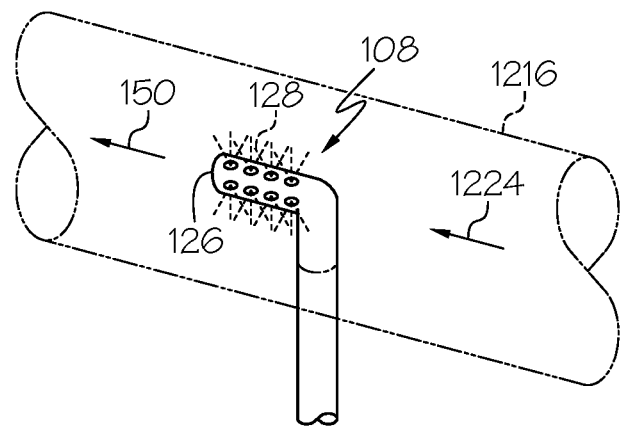
FIG. 8 is a schematic illustration of an example of a piccolo nozzle of the disinfectant dispenser of the disinfecting system.

Referring to FIGS. 3 and 8, in one or more examples of the disinfecting system 100 and/or the aircraft 1200, the at least one disinfectant dispenser 108 includes, or takes the form of, a piccolo nozzle 126, also referred to as a piccolo-tube nozzle. In one or more examples, the piccolo nozzle 126 includes, or takes the form of, a closed-end tube, or pipe, having a plurality of orifices through which a gas is dispensed. In these examples, the piccolo nozzle 126 facilitates dispersal of the disinfectant 104 in gaseous form (e.g., the gas 128) into the air 1224 to form the mixture 150.

In other examples, different types of suitable gas-dispensing nozzles or gas-dispersal nozzles are also contemplated.

In one or more examples of the aircraft 1200, the disinfectant 104 (e.g., the gas 128) includes, or takes the form of, ozone 140. In one or more examples, the aircraft 1200 includes a catalytic converter 138. The catalytic converter 138 is configured to convert the disinfectant 104 (e.g., ozone 140) in the air 1224 within the interior 1206 to oxygen. Use of the catalytic converter 138 may increase the rate that the disinfectant 104 is purged from within the interior 1206.

Referring to FIG. 3, in one or more examples of the disinfecting system 100 and/or the aircraft 1200, the disinfectant 104 is a liquid 130. The disinfectant delivery device 106 includes, or takes the form of, a pump 132. In one or more examples, the disinfectant 104 includes any suitable liquid disinfecting material, such as at least one of a chemical-based liquid disinfectant, a hydrogen peroxide-based disinfectant, a bleach-based disinfectant, and the like. In one or more examples, the pump 132 includes any suitable liquid moving device.

Figure 6:
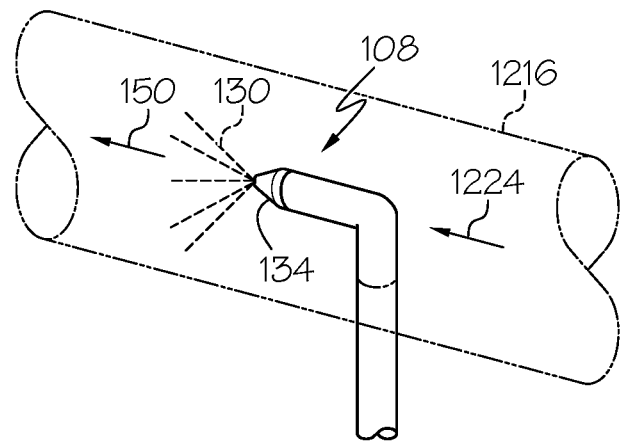
FIG. 6 is a schematic illustration of an example of an atomizing nozzle of a disinfectant dispenser of the disinfecting system.

Referring to FIGS. 3 and 6, in one or more examples of the disinfecting system 100 and/or the aircraft 1200, the at least one disinfectant dispenser 108 includes, or takes the form of, an atomizing nozzle 134, also referred to as an atomizer nozzle or aspirator nozzle. In one or more examples, the atomizing nozzle 134 is configured to atomize a liquid (e.g., the disinfecting liquid 130) by creating a fine spray. In these examples, the atomizing nozzle 134 facilitates dispersal of the disinfectant 104 in liquid form (e.g., the liquid 130) into the air 1224 to form the mixture 150. For example, the disinfectant 104 in liquid form (e.g., the liquid 130) and compressed air may be used to produce a mist of atomized liquid at low pressure.

Figure 7:
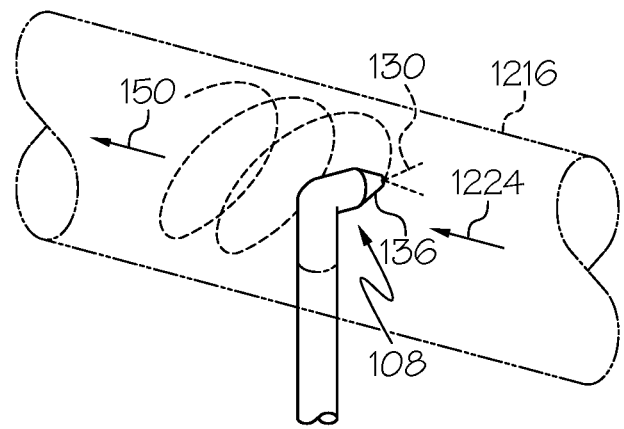
FIG. 7 is a schematic illustration of an example of a swirl nozzle of the disinfectant dispenser of the disinfecting system.

Referring to FIGS. 3 and 7, in one or more examples of the disinfecting system 100 and/or the aircraft 1200, the at least one disinfectant dispenser 108 includes, or takes the form of, a swirl nozzle 136, also referred to as a pressure-swirl nozzle. In one or more examples, the swirl nozzle 136 is configured to produce a small drop size and includes a stationary core that induces a rotary fluid motion, which causes swirling of the disinfectant 104 in liquid form (e.g., the liquid 130) in a swirl chamber. A film is discharged from a perimeter of an outlet orifice producing a characteristic hollow cone spray pattern. Air or other surrounding gas is drawn inside the swirl chamber to form an air core within the swirling liquid. Many configurations of fluid inlets may be used to produce the hollow cone pattern depending on the nozzle capacity and materials of construction. In these examples, the swirl nozzle 136 facilitates dispersal of the disinfectant 104 in liquid form (e.g., the liquid 130) into air 1224 to form the mixture 150.

In other examples, different types of suitable liquid-dispensing nozzles or liquid-dispersal nozzles are also contemplated.

Referring generally to FIGS. 1-4 and 6-8, by way of examples, the present disclosure is also directed the disinfecting system 100 for rapidly and efficiently disinfecting the interior 1206 of the aircraft 1200. In one or more examples, the disinfecting system 100 is located within, is integrated with, or forms a portion of the aircraft 1200. In one or more examples, the disinfecting system 100 is located within, is integrated with, or forms a portion of the environmental system 1214. In one or more examples, the disinfecting system 100 is a standalone system that is appropriately situated within the aircraft 1200 and/or the environmental system 1214 for performance of the disinfecting operation.

Referring again to FIGS. 3 and 4, in one or more examples, the disinfecting system 100 includes the disinfectant supply 102 configured store the disinfectant 104. The disinfecting system 100 also includes at least one disinfectant dispenser 108 in fluid communication with the disinfectant supply 102 and configured to dispense the disinfectant 104 in the air 1224 circulated through the interior 1206 by the environmental system 1214.

In one or more examples of the disinfecting system 100, the at least one disinfectant dispenser 108 is located within the air supply duct 1216 of the environmental system 1214 to dispense the disinfectant 104 directly into the airstream 1228 within the air supply duct 1216.

In one or more examples, the disinfecting system 100 includes the at least one sensor 144 configured to detect one or more conditions of the interior 1206 of the aircraft 1200. The disinfecting system 100 also includes the disinfectant controller 120 configured to selectively control dispensation of the disinfectant 104 from the at least one disinfectant dispenser 108 based on the one or more conditions detected by the at least one sensor 144.

In one or more examples of the disinfecting system 100, the one or more conditions includes at least one of occupancy of the interior 1206 and the concentration of the disinfectant 104 in the air 1224. In other examples, the one or more conditions include any other measurable or determinable condition, such as internal pressure within the interior, a circulation rate of the air 1224 through the interior 1206, and the like.

In one or more examples of the disinfecting system 100, the at least one disinfectant dispenser 108 includes the plurality of disinfectant dispensers 108. The disinfecting system 100 includes the disinfectant delivery device 106 in fluid communication with the plurality of disinfectant dispensers 108. The disinfecting system 100 also includes the distribution manifold 110 in fluid communication with the disinfectant delivery device 106 and with the plurality of disinfectant dispensers 108. The distribution manifold 110 is configured to distribute the disinfectant 104 to each one of the plurality of disinfectant dispensers 108

In one or more examples, the disinfecting system 100 includes the disinfectant delivery device 106 in fluid communication with the disinfectant supply 102 and with the at least one disinfecting dispenser 108. The disinfecting delivery device 106 is configured to deliver the disinfectant 104 to the at least one disinfecting dispenser 108.

In one or more examples, the disinfecting system 100 includes the metering device 142 located between and in fluid communication with the disinfectant delivery device 106 and with the at least one disinfectant dispenser 108. The metering device 142 is configured to selectively control the quantity of the disinfectant 104 delivered to the at least one disinfectant dispenser 108.

In one or more examples, the disinfecting system 100 includes the disinfectant controller 120 in communication with the disinfectant delivery device 106 and configured to selectively initiate or selectively terminate delivery of the disinfectant 104 from the disinfectant delivery device 106 to the at least one disinfectant dispenser 108.

In one or more examples, the disinfecting system 100 includes the occupancy sensor 112 in communication with the disinfectant controller 120 and configured to generate an occupancy signal 114 that indicates whether the interior 1206 of the aircraft 1200 is occupied.

In one or more examples, the disinfecting system 100 includes the concentration sensor 116 in communication with the disinfectant controller 120 and configured to generate a concentration signal 118 that indicates a concentration of the disinfectant 104 in the air 1224 within the interior 1206 of the aircraft 1200.

In one or more examples of the disinfecting system 100, the disinfectant controller 120 is configured to determine the concentration of the disinfectant 104 in the air 1224 within the interior 1206 of the aircraft 1200 based on the interior volume 1230 of the interior 1206 and the circulation rate of the air 1224 through the interior 1206.

In one or more examples of the disinfecting system 100, the disinfectant controller 120 is in communication with the air handling device 1218 of the environmental system 1214, configured to generate the airstream 1228 that circulates the air 1224 through the interior 1206, and is configured to selectively activate or selectively deactivate the air handling device 1218.

In one or more examples of the disinfecting system 100, at least one disinfectant dispenser 108 is located within at least one of the plurality of air supply ducts 1216 of the environmental system 1214, which is in fluid communication with the air handling device 1218, to dispense the disinfectant 104 directly into the airstream 1228 within the at least one of the plurality of air supply ducts 1216.

In one or more examples of the disinfecting system 100 at least one disinfectant dispenser 108 is located upstream from the plurality of air supply outlets 1226 of the plurality of air supply ducts 1216.

In one or more examples, the disinfecting system 100 includes the plurality of disinfectant dispensers 108. The disinfecting system 100 also includes the distribution manifold 110 in fluid communication with the disinfectant delivery device 106 and with the plurality of disinfectant dispensers 108. The distribution manifold 110 is configured to distribute the disinfectant 104 to each one of the plurality of disinfectant dispensers 108.

In one or more examples of the disinfecting system 100, each one of the plurality of disinfectant dispensers 108 corresponds to one of the plurality of air supply outlets 1226 of the plurality of air supply ducts 1216. At least one of the plurality of disinfectant dispensers 108 is located within each one of the plurality of air supply ducts 1216 upstream from a corresponding one of the plurality of air supply outlets 1226 to dispense the disinfectant 104 directly into the airstream 1228 within each one of the plurality of air supply ducts 1216.

In one or more examples, the disinfecting system 100 includes the mixing manifold 1232 that is located between and that is in fluid communication with the air handling device 1218 and with the plurality of air supply ducts 1216. The at least one disinfectant dispenser 108 is located within the mixing manifold 1232 to dispense the disinfectant 104 directly into the airstream 1228 within the mixing manifold 1232.

In one or more examples of the disinfecting system 100, the at least one disinfectant dispenser 108 is coupled to the floor 1220 of the interior 1206 of the aircraft 1200 to dispense the disinfectant 104 directly into the air 1224 within the interior 1206.

In one or more examples of the disinfecting system 100, the disinfectant controller 120 is in communication with the plurality of circulation fans 1222 of the aircraft 1200 and is configured to selectively activate or selectively deactivate each one of the plurality of circulation fans 1222.

In one or more examples, the disinfecting system 100 includes the disinfectant supply 102 configured to store the disinfectant 104 and in fluid communication with the disinfectant delivery device 106. In one or more examples, a regulator 152 (e.g., as shown in FIG. 4) is coupled between and is in fluid communication with the disinfectant supply 102 and the disinfectant delivery device 106. The regulator 152 is configured to selectively control the flow of the disinfectant 104 from the disinfectant supply 102. In one or more examples, the disinfectant controller 120 is in communication with the regulator 152 to selectively control the flow of the disinfectant 104. In one or more examples, additional components, such as pumps, valves, restrictors, and the like maybe used to transfer the disinfectant 104.

In one or more examples of the disinfecting system 100, the disinfectant supply 102 is located within the interior 1206 of the aircraft 1200.

In one or more examples, the disinfecting system 100 includes the disinfectant connection port 148 coupled to the aircraft 1200, outside of the interior 1206 of the aircraft 1200, and in fluid communication with the disinfectant delivery device 106. The disinfectant supply 102 is located outside of the interior 1206 of the aircraft 1200 and is configured to be fluidly coupled with the disinfectant connection port 148.

In one or more examples of the disinfecting system 100 the disinfectant 104 is the gas 128. The disinfectant delivery device 106 includes, or takes the form of, the fan 124.

In one or more examples of the disinfecting system 100, at least one disinfectant dispenser 108 includes, or takes the form of, the piccolo nozzle 126.

In one or more examples of the disinfecting system 100, the disinfectant 104 includes, or takes the form of, ozone 140.

In one or more examples, the disinfecting system 100 includes the catalytic converter 138 configured to convert the disinfectant 104 (e.g., ozone 140) in the air 1224 within the interior 1206 to oxygen.

In one or more examples of the disinfecting system 100, the disinfectant 104 is the liquid 130. The disinfectant delivery device 106 includes, or takes the form of, the pump 132.

In one or more examples of the disinfecting system 100, at least one disinfectant dispenser 108 includes, or takes the form of, the atomizing nozzle 134.

In one or more examples of the disinfecting system 100, at least one disinfectant dispenser 108 includes, or takes the form of, the swirl nozzle 136.

Figure 5:
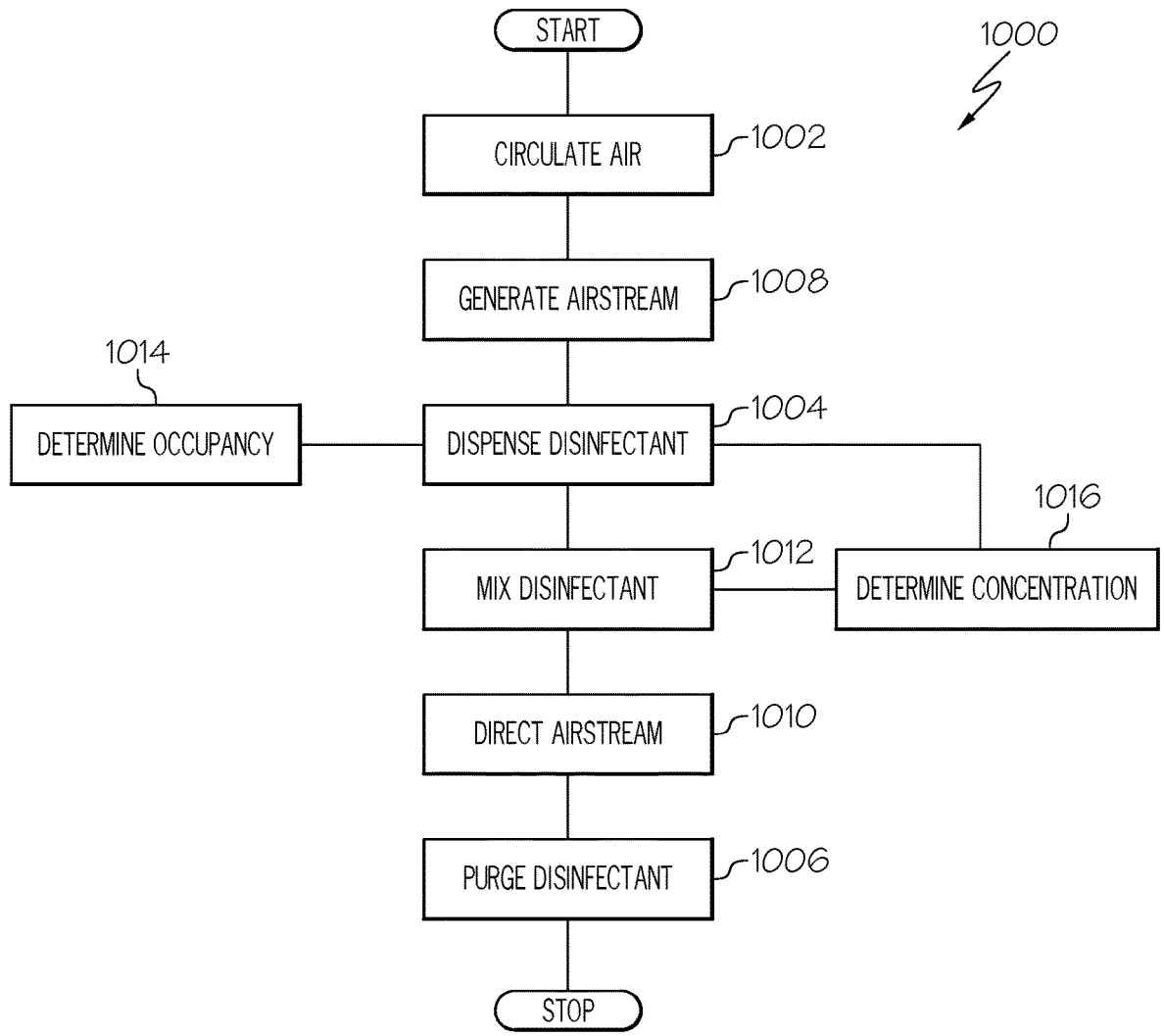
FIG. 5 is a flow diagram of an example of a method of disinfecting an interior of an aircraft.

Referring generally to FIGS. 1-4 and 6-8, and particularly to FIG. 5, by way of examples, the present disclosure is also directed to a method 1000 of disinfecting the interior 1206 of the aircraft 1200. In one or more examples, the method 1000 is implemented and performed utilizing the disinfecting system 100.

In one or more examples, method 1000 includes a step of (block 1002) circulating air 1224 through the interior 1206 of the aircraft 1200. The method 1000 also includes a step of (block 1004) dispensing the disinfectant 104 in the air 1224 circulated through the interior 1206. The method 1000 further includes a step of (block 1006), upon a predetermined condition, purging the disinfectant 104 from the interior 1206.

In one or more examples, in accordance with the method 1000, the step of (block 1002) circulating the air 1224 through the interior 1206 includes, or is achieved by, a step of (block 1008) generating the airstream 1228 and a step of (block 1010) directing the airstream 1228 within the interior 1206.

In one or more examples, the method 1000 includes a step of (block 1012) mixing the disinfectant 104 with the air 1224 to form the mixture 150.

In one or more examples, in accordance with the method 1000, the step of (block 1004) dispensing the disinfectant 104 into the air 1224 includes a step of dispensing the disinfectant 104 directly into the airstream 1228. In accordance with the method 1000, the step of (block 1012) mixing the disinfectant 104 includes a step of mixing the disinfectant 104 with the airstream 1228 before directing the airstream 1228 within the interior 1206.

In one or more examples, in accordance with the method 1000, the step of (block 1004) dispensing the disinfectant 104 into the air 1224 includes a step of dispensing the disinfectant 104 within the interior 1206 after directing the airstream 1228 within the interior 1206. In accordance with the method 1000, the step of (block 1012) mixing the disinfectant 104 includes a step of mixing the disinfectant 104 with the airstream 1228 after directing the airstream 1228 within the interior 1206.

In one or more examples, the method 1000 includes a step of (block 1014) determining occupancy of the aircraft 1200, such as determining that the interior 1206 is unoccupied before dispensing the disinfectant 104 in the air 1224.

In one or more examples, the method 1000 includes a step of (block 1016) determining the concentration of the disinfectant 104 in the air 1224 within the interior 1206.

In one or more examples, in accordance with the method 1000, the predetermined condition includes achieving a predetermined concentration of the disinfectant 104 in the air 1224.

In one or more examples, in accordance with the method 1000, the predetermined condition includes achieving a predetermined pressure within the interior 1206.

In one or more examples, in accordance with the method 1000, the predetermined condition includes achieving a predetermined period.

In one or more examples, the step of (block 1006), upon a predetermined condition, purging the disinfectant 104 from the interior 1206 involves detecting the predetermined condition and purging the disinfectant 104 from the interior 1206 in response to detecting the predetermined condition.

In one or more examples, the method 1000 includes a step of terminating interior circulation of the air 1224 within the interior 1206 before dispensing the disinfectant 104 in the air 1224. For example, one or more of the circulation fans 1222 may be deactivated to prevent the disinfectant 104 from entering undesirable areas of the interior 1206.

In one or more examples, in accordance with the method 1000, the step of (block 1006) purging the disinfectant 104 from the interior 1206 includes a step of terminating the dispensing of the disinfectant 104 and a step of continuing to circulate the air 1224 through the interior 1206. Directing the airstream 1228, without the disinfectant 104, into the interior 1206 fills the interior 1206 with the air 1224, thus reducing the concentration of the disinfectant 104 and/or pushing the disinfectant mixture 150 out of the interior 1206 as the air 1224 fills the interior 1206. Purging the disinfectant 104 continues until the concentration of the disinfectant 104 in the area is reduced to below a predetermined threshold.

Accordingly, examples of the disclosed aircraft 1200, disinfecting system 100, and method 1000 facilitate injection of the disinfectant 104 (e.g., gas or liquid) directly into the interior 1206 of the aircraft 1200 through the air supply of the environmental control system 1214. In one or more examples, the disinfecting operation is automatic. For example, the plurality of sensors 144 detect whether the interior 1206 is empty and detect when enough disinfectant 104 is present in the air 1224 to adequately disinfect the contact surfaces 1240. The disinfecting system 100 fills at least a portion of the interior 1206 with the disinfectant mixture 150 (the gaseous mixture of the disinfectant 104 and the air 1224). The disinfecting system 100 then purges the disinfectant mixture 150 out of interior 1206. The plurality of sensors 144 also detect that the disinfectant mixture 150 is purged from interior 1206 and generate an indicator that the interior 1206 is safe for re-entry.

In one or more examples, the disinfectant controller 120 is configured to control all or some of the circulation fans 1222 of the aircraft 1200 to ensure that the disinfectant 104 adequately fills the interior 1206 and to ensure that the disinfectant 104 is not directed into areas of the interior 1206 that house electronic systems and to prevent the disinfectant 104 from going into equipment racks. In one or more examples, the disinfectant controller 120 is also configured to control other fans for filters to prevent the disinfectant 104 from building up in the filters.

In one or more examples, the disinfecting system 100 is an original equipment manufacturer (OEM) component of the aircraft 1200. In one or more examples, the aircraft 1200 is retrofitted to include the disinfecting system 100.

Referring now to FIGS. 1 and 9, examples of the disinfecting system 100 and the method 1000 may be related to, or used in the context of, an aircraft manufacturing and service method 1100, as shown in the flow diagram of FIG. 9 and the aircraft 1200, as schematically illustrated in FIG. 1.

Referring to FIG. 9, during pre-production, the method 1100 includes specification and design of the aircraft 1200 (block 1102) and material procurement (block 1104). During production of the aircraft 1200, component and subassembly manufacturing (block 1106) and system integration (block 1108) of the aircraft 1200 take place. Thereafter, the aircraft 1200 goes through certification and delivery (block 1110) to be placed in service (block 1112). Routine maintenance and service (block 1114) includes modification, reconfiguration, refurbishment, etc. of one or more systems of the aircraft 1200.

Figure 9:
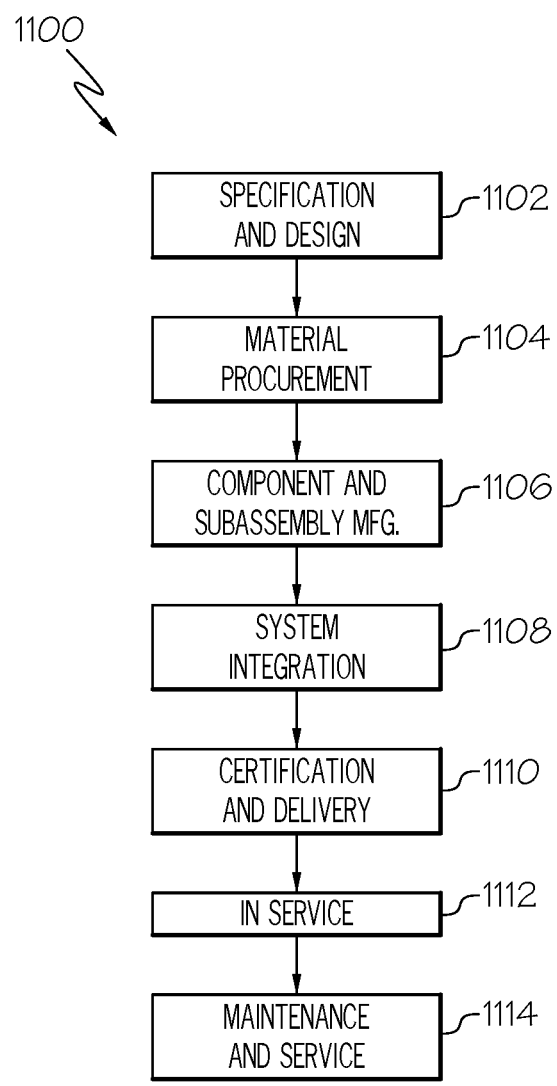
FIG. 9 is a flow diagram of an aircraft manufacturing and service methodology.

Each of the processes of the method 1100 illustrated in FIG. 9 may be performed or carried out by a system integrator, a third party, and/or an operator (e.g., a customer). For the purposes of this description, a system integrator may include, without limitation, any number of spacecraft manufacturers and major-system subcontractors; a third party may include, without limitation, any number of vendors, subcontractors, and suppliers; and an operator may be an airline, leasing company, military entity, service organization, and so on.

Examples of the aircraft 1200, the disinfecting system 100, and the method 1000 shown and described herein may be employed during any one or more of the stages of the manufacturing and service method 1100 shown in the flow diagram illustrated by FIG. 9. In an example, implementations of the disclosed aircraft 1200, the disinfecting system 100, and the method 1000 may form a portion of component and subassembly manufacturing (block 1106) and/or system integration (block 1108). For example, disinfecting the interior 1206 of the aircraft 1200 and/or components thereof using implementations of the disclosed disinfecting system 100 and method 1000 may correspond to component and subassembly manufacturing (block 1106) and may be utilized in a manner similar to components or subassemblies prepared while the aircraft 1200 is in service (block 1112). Also, implementations of the disclosed disinfecting system 100 and the method 1000 may be utilized during system integration (block 1108) and certification and delivery (block 1110). Similarly, implementations of the disclosed disinfecting system 100 and the method 1000 may be utilized, for example and without limitation, while the aircraft 1200 is in service (block 1112) and during maintenance and service (block 1114).

Although an aerospace example is shown, the examples and principles disclosed herein may be applied to other industries, such as the automotive industry, the space industry, the construction industry, and other design and manufacturing industries. Accordingly, in addition to aircraft, the examples and principles disclosed herein may apply to systems for disinfecting an interior of other types of vehicles (e.g., land vehicles, marine vehicles, space vehicles, etc.) and stand-alone structures.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, device, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, device, structure, article, element, component, or hardware described as being "configured to" perform a particular function may additionally or alternatively be described as being "adapted to" and/or as being "operative to" perform that function.

Unless otherwise indicated, the terms "first," "second," "third," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations.

For the purpose of this disclosure, the terms "coupled," "coupling," and similar terms refer to two or more elements that are joined, linked, fastened, attached, connected, put in communication, or otherwise associated (e.g., mechanically, electrically, fluidly, optically, electromagnetically) with one another. In various examples, the elements may be associated directly or indirectly. As an example, element A may be directly associated with element B. As another example, element A may be indirectly associated with element B, for example, via another element C. It will be understood that not all associations among the various disclosed elements are necessarily represented. Accordingly, couplings other than those depicted in the figures may also exist.

As used herein, the term "approximately" refers to or represent a condition that is close to, but not exactly, the stated condition that still performs the desired function or achieves the desired result. As an example, the term "approximately" refers to a condition that is within an acceptable predetermined tolerance or accuracy, such as to a condition that is within 10% of the stated condition. However, the term "approximately" does not exclude a condition that is exactly the stated condition. As used herein, the term "substantially" refers to a condition that is essentially the stated condition that performs the desired function or achieves the desired result.

In FIGS. 3 and 4, referred to above, the blocks may represent functional elements, features, or components thereof and lines connecting the various blocks do not necessarily imply any particular structure. Accordingly, modifications, additions and/or omissions may be made to the illustrated structure. Additionally, those skilled in the art will appreciate that not all elements described and illustrated in FIGS. 1-4 and 6-8, referred to above, need be included in every example and not all elements described herein are necessarily depicted in each illustrative example. Unless otherwise explicitly stated, the schematic illustrations of the examples depicted in FIGS. 1-4 and 6-8, referred to above, are not meant to imply structural limitations with respect to the illustrative example. Rather, although one illustrative structure is indicated, it is to be understood that the structure may be modified when appropriate.

In FIGS. 5 and 9, referred to above, the blocks may represent operations, steps, and/or portions thereof and lines connecting the various blocks do not imply any particular order or dependency of the operations or portions thereof. It will be understood that not all dependencies among the various disclosed operations are necessarily represented. FIGS. 5 and 9 and the accompanying disclosure describing the operations of the disclosed methods set forth herein should not be interpreted as necessarily determining a sequence in which the operations are to be performed. Rather, although one illustrative order is indicated, it is to be understood that the sequence of the operations may be modified when appropriate. Accordingly, modifications, additions and/or omissions may be made to the operations illustrated and certain operations may be performed in a different order or simultaneously. Additionally, those skilled in the art will appreciate that not all operations described need be performed.

Further, references throughout the present specification to features, advantages, or similar language used herein do not imply that all of the features and advantages that may be realized with the examples disclosed herein should be, or are in, any single example. Rather, language referring to the features and advantages is understood to mean that a specific feature, advantage, or characteristic described in connection with an example is included in at least one example. Thus, discussion of features, advantages, and similar language used throughout the present disclosure may, but do not necessarily, refer to the same example.

Further, the disclosure comprises embodiments according to the following clauses:

Clause 1. An aircraft comprising:
an interior;
an environmental system configured to circulate air through the interior; and
at least one disinfectant dispenser configured to dispense a disinfectant in the air circulated through the interior.

Clause 2. The aircraft of Clause 1, wherein the at least one disinfectant dispenser is located within an air supply duct of the environmental system to dispense the disinfectant directly into an airstream within the air supply duct.

Clause 3. The aircraft of Clause 1 or Clause 2, further comprising:
at least one sensor configured to detect one or more conditions of the interior; and
a disinfectant controller configured to selectively control dispensation of the disinfectant from the at least one disinfectant dispenser based on the one or more conditions detected by the at least one sensor.

Clause 4. The aircraft of Clause 3, wherein the one or more conditions comprise at least one of occupancy of the interior and concentration of the disinfectant in the air.

Clause 5. The aircraft of any of Clauses 1 to 4, wherein:
the at least one disinfectant dispenser comprises a plurality of disinfectant dispensers;
the aircraft further comprises:
a disinfectant delivery device in fluid communication with the plurality of disinfectant dispensers; and
a distribution manifold in fluid communication with the disinfectant delivery device and with the plurality of disinfectant dispensers; and
the distribution manifold is configured to distribute the disinfectant to each one of the plurality of disinfectant dispensers.

Clause 6. The aircraft of any of Clauses 1 to 5, further comprising a disinfectant delivery device in fluid communication with the at least one disinfectant dispenser, wherein the disinfecting delivery device is configured to deliver the disinfectant to the at least one disinfectant dispenser.

Clause 7. The aircraft of Clause 6, further comprising a metering device located between and in fluid communication with the disinfectant delivery device and with the at least one disinfectant dispenser, wherein the metering device is configured to selectively control a quantity of the disinfectant delivered to the at least one disinfectant dispenser.

Clause 8. The aircraft of Clause 6 or Clause 7, further comprising a disinfectant controller in communication with the disinfectant delivery device and configured to selectively initiate or selectively terminate delivery of the disinfectant from the disinfectant delivery device to the at least one disinfectant dispenser.

Clause 9. The aircraft of Clause 8, further comprising an occupancy sensor in communication with the disinfectant controller and configured to generate an occupancy signal that indicates whether the interior is occupied.

Clause 10. The aircraft of Clause 8 or Clause 9, further comprising a concentration sensor in communication with the disinfectant controller and configured to generate a concentration signal that indicates a concentration of the disinfectant in the air within the interior.

Clause 11. The aircraft of any of Clauses 8 to 10, wherein the disinfectant controller is configured to determine a concentration of the disinfectant in the air within the interior based on an interior volume of the interior and a circulation rate of the air through the interior.

Clause 12. The aircraft of any of Clauses 8 to 11, wherein:
the environmental system comprises an air handling device configured to generate an airstream that circulates the air through the interior; and
the disinfectant controller is in communication with the air handling device and is configured to selectively activate or selectively deactivate the air handling device.

Clause 13. The aircraft of Clause 12, wherein:
the air handling device comprises a variable speed fan; and
the disinfectant controller is configured to, in response to a predetermined condition, increase a speed of the variable speed fan so as to purge the disinfectant from the interior.

Clause 14. The aircraft of Clause 12 or Clause 13, wherein:
the environmental system further comprises air supply ducts in fluid communication with the air handling device and configured to direct the airstream within the interior; and
the at least one disinfectant dispenser is located within at least one of the air supply ducts to dispense the disinfectant directly into the airstream within the air supply ducts.

Clause 15. The aircraft of Clause 14, wherein:
the air supply ducts comprise a plurality of air supply outlets located in the interior; and
the at least one disinfectant dispenser is located upstream from the plurality of air supply outlets.

Clause 16. The aircraft of Clause 15, wherein:
the air supply ducts have an inner diameter; and
the at least one disinfectant dispenser is located upstream from any one of the plurality of air supply outlets by a distance of at least five times the inner diameter.

Clause 17. The aircraft of any of Clauses 14 to 16, further comprising:
a plurality of disinfectant dispensers; and
a distribution manifold in fluid communication with the disinfectant delivery device and with the plurality of disinfectant dispensers, wherein the distribution manifold is configured to distribute the disinfectant to each one of the plurality of disinfectant dispensers.

Clause 18. The aircraft of Clause 17, wherein:
the air supply ducts comprise a plurality of air supply outlets located in the interior;
at least one of the plurality of disinfectant dispensers corresponds to one of plurality of air supply outlets; and each one of the plurality of disinfectant dispensers is located within each one of the air supply ducts upstream from a corresponding one of the plurality of air supply outlets to dispense the disinfectant directly into the airstream within each one of the air supply ducts.

Clause 19. The aircraft of any of Clauses 14 to 18, further comprising a mixing manifold that is located between and that is in fluid communication with the air handling device and with the air supply ducts, wherein the at least one disinfectant dispenser is located within the mixing manifold to dispense the disinfectant directly into the airstream within the mixing manifold.

Clause 20. The aircraft of Clause 12 or Clause 13, wherein:
the interior comprises a floor; and
the at least one disinfectant dispenser is coupled to the floor to dispense the disinfectant directly into the air within the interior.

Clause 21. The aircraft of any of Clauses 8 to 20, further comprising a plurality of circulation fans located within the interior, wherein the disinfectant controller is in communication with the plurality of circulation fans and is configured to selectively activate or selectively deactivate each one of the plurality of circulation fans.

Clause 22. The aircraft of any of Clauses 6 to 21, further comprising a disinfectant supply configured to store the disinfectant and in fluid communication with the disinfectant delivery device.

Clause 23. The aircraft of Clause 22, wherein the disinfectant supply is located within the interior.

Clause 24. The aircraft of Clause 22, further comprising a disinfectant connection port located outside of the interior and in fluid communication with the disinfectant delivery device, wherein the disinfectant supply is located outside of the interior and is configured to be fluidly coupled with the disinfectant connection port.

Clause 25. The aircraft of any of Clauses 6 to 24, wherein:
the disinfectant is a gas; and
the disinfectant delivery device comprises a fan.

Clause 26. The aircraft of Clause 25, wherein the at least one disinfectant dispenser comprises a piccolo nozzle.

Clause 27. The aircraft of Clause 25 or Clause 26, wherein the disinfectant comprises ozone.

Clause 28. The aircraft of Clause 27, further comprising a catalytic converter configured to convert the disinfectant in the air within the interior to oxygen.

Clause 29. The aircraft of any of Clauses 6 to 24, wherein:
the disinfectant is a liquid; and
the disinfectant delivery device comprises a pump.

Clause 30. The aircraft of Clause 29, wherein the at least one disinfectant dispenser comprises an atomizing nozzle.

Clause 31. The aircraft of Clause 29 or Clause 30, wherein the at least one disinfectant dispenser comprises a swirl nozzle.

Clause 32. A disinfecting system for an aircraft, comprising an interior and an environmental system, the disinfecting system comprising:
a disinfectant supply configured store a disinfectant; and
at least one disinfectant dispenser in fluid communication with the disinfectant supply and configured to dispense the disinfectant in air circulated through the interior by the environmental system.

Clause 33. The disinfecting system of Clause 32, wherein the at least one disinfectant dispenser is located within an air supply duct of the environmental system to dispense the disinfectant directly into an airstream within the air supply duct.

Clause 34. The disinfecting system of Clause 32 or Clause 33, further comprising:
at least one sensor configured to detect one or more conditions of the interior of the aircraft; and
a disinfectant controller configured to selectively control dispensation of the disinfectant from the at least one disinfectant dispenser based on the one or more conditions detected by the at least one sensor.

Clause 35. The disinfecting system of Clause 34, wherein the one or more conditions comprise at least one of occupancy of the interior and concentration of the disinfectant in the air.

Clause 36. The disinfecting system of any of Clauses 32 to 35, wherein:
the at least one disinfectant dispenser comprises a plurality of disinfectant dispensers;
the disinfecting system further comprises:
a disinfectant delivery device in fluid communication with the plurality of disinfectant dispensers; and
a distribution manifold in fluid communication with the disinfectant delivery device and with the plurality of disinfectant dispensers; and
the distribution manifold is configured to distribute the disinfectant to each one of the plurality of disinfectant dispensers.

Clause 37. The disinfecting system of any of Clauses 32 to 36, further comprising a disinfectant delivery device in fluid communication with the disinfectant supply and with the at least one disinfecting dispenser, wherein the disinfecting delivery device is configured to deliver the disinfectant to the at least one disinfecting dispenser.

Clause 38. The disinfecting system of Clause 37, further comprising a metering device located between and in fluid communication with the disinfectant delivery device and with the at least one disinfectant dispenser, wherein the metering device is configured to selectively control a quantity of the disinfectant delivered to the at least one disinfectant dispenser.

Clause 39. The disinfecting system of Clause 37 or Clause 38, further comprising a disinfectant controller in communication with the disinfectant delivery device and configured to selectively initiate or selectively terminate delivery of the disinfectant from the disinfectant delivery device to the at least one disinfectant dispenser.

Clause 40. The disinfecting system of Clause 39, further comprising an occupancy sensor in communication with the disinfectant controller and configured to generate an occupancy signal that indicates whether the interior of the aircraft is occupied.

Clause 41. The disinfecting system of Clause 39 or Clause 40, further comprising a concentration sensor in communication with the disinfectant controller and configured to generate a concentration signal that indicates a concentration of the disinfectant in the air within the interior of the aircraft.

Clause 42. The disinfecting system of any of Clauses 39 to 41, wherein the disinfectant controller is configured to determine a concentration of the disinfectant in the air within the interior of the aircraft based on an interior volume of the interior and a circulation rate of the air through the interior.

Clause 43. The disinfecting system of any of Clauses 39 to 42, wherein the disinfectant controller is in communication with an air handling device of the environmental system, configured to generate an airstream that circulates the air through the interior, and is configured to selectively activate or selectively deactivate the air handling device.

Clause 44. The disinfecting system of Clause 43, wherein the at least one disinfectant dispenser is located within at least one of a plurality of air supply ducts of the environmental system, in fluid communication with the air handling device, to dispense the disinfectant directly into the airstream within the at least one of the plurality of air supply ducts.

Clause 45. The disinfecting system of Clause 44, wherein the at least one disinfectant dispenser is located upstream from a plurality of air supply outlets of the plurality of air supply ducts.

Clause 46. The disinfecting system of Clause 44 or Clause 45, further comprising:
 a plurality of disinfectant dispensers; and
 a distribution manifold in fluid communication with the disinfectant delivery device and with the plurality of disinfectant dispensers, wherein the distribution manifold is configured to distribute the disinfectant to each one of the plurality of disinfectant dispensers.

Clause 47. The disinfecting system of Clause 46, wherein:
 each one of the plurality of disinfectant dispensers corresponds to one of a plurality of air supply outlets of the plurality of air supply ducts; and
 at least one of the plurality of disinfectant dispensers is located within each one of the plurality of air supply ducts upstream from a corresponding one of the plurality of air supply outlets to dispense the disinfectant directly into the airstream within each one of the plurality of air supply ducts.

Clause 48. The disinfecting system of any of Clauses 44 to 47, further comprising a mixing manifold that is located between and that is in fluid communication with the air handling device and with the plurality of air supply ducts, wherein the at least one disinfectant dispenser is located within the mixing manifold to dispense the disinfectant directly into the airstream within the mixing manifold.

Clause 49. The disinfecting system of Clause 43, wherein the at least one disinfectant dispenser is coupled to a floor of the interior of the aircraft to dispense the disinfectant directly into the air within the interior.

Clause 50. The disinfecting system of any of Clauses 39 to 49, wherein the disinfectant controller is in communication with a plurality of circulation fans of the aircraft and is configured to selectively activate or selectively deactivate each one of the plurality of circulation fans.

Clause 51. The disinfecting system of any of Clauses 37 to 50, further comprising a disinfectant supply configured to store the disinfectant and in fluid communication with the disinfectant delivery device.

Clause 52. The disinfecting system of Clause 51, wherein the disinfectant supply is located within the interior of the aircraft.

Clause 53. The disinfecting system of Clause 51, further comprising a disinfectant connection port coupled to the aircraft, outside of the interior of the aircraft, and in fluid communication with the disinfectant delivery device, wherein the disinfectant supply is located outside of the interior of the aircraft and is configured to be fluidly coupled with the disinfectant connection port.

Clause 54. The disinfecting system of any of Clauses 37 to 53, wherein:
 the disinfectant is a gas; and
 the disinfectant delivery device comprises a fan.

Clause 55. The disinfecting system of Clause 54, wherein the at least one disinfectant dispenser comprises a piccolo nozzle.

Clause 56. The disinfecting system of Clause 54 or Clause 55, wherein the disinfectant comprises ozone.

Clause 57. The disinfecting system of Clause 56, further comprising a catalytic converter configured to convert the disinfectant in the air within the interior to oxygen.

Clause 58. The disinfecting system of Clauses 37 to 53, wherein:
 the disinfectant is a liquid; and
 the disinfectant delivery device comprises a pump.

Clause 59. The disinfecting system of Clause 58, wherein the at least one disinfectant dispenser comprises an atomizing nozzle.

Clause 60. The disinfecting system of Clause 58 or Clause 59, wherein the at least one disinfectant dispenser comprises a swirl nozzle.

Clause 61. A method of disinfecting an interior of an aircraft, the method comprising:
 circulating air through the interior of the aircraft;
 dispensing a disinfectant in the air circulated through the interior; and
 upon a predetermined condition, purging the disinfectant from the interior.

Clause 62. The method of Clause 61, wherein circulating the air through the interior comprises:
 generating an airstream; and
 directing the airstream within the interior.

Clause 63. The method of Clause 62, wherein dispensing the disinfectant into the air comprises dispensing the disinfectant directly into the airstream.

Clause 64. The method of Clause 63, further comprising mixing the disinfectant with the airstream before directing the airstream within the interior.

Clause 65. The method of Clause 62, wherein dispensing the disinfectant into the air comprises dispensing the disinfectant within the interior after directing the airstream within the interior.

Clause 66. The method of any of Clauses 61 to 65, further comprising determining that the interior is unoccupied before dispensing the disinfectant in the air.

Clause 67. The method of any of Clauses 61 to 66, wherein the predetermined condition comprises achieving a predetermined concentration of the disinfectant in the air.

Clause 68. The method of any of Clauses 61 to 66, wherein the predetermined condition comprises achieving a predetermined pressure within the interior.

Clause 69. The method of any of Clauses 61 to 66, wherein the predetermined condition comprises achieving a predetermined period.

Clause 70. The method of any of Clauses 61 to 69, further comprising terminating interior circulation of the air within the interior before dispensing the disinfectant in the air.

Clause 71. The method of any of Clauses 61 to 70, wherein purging the disinfectant from the interior comprises:

terminating the dispensing of the disinfectant; and continuing to circulate the air through the interior.

The described features, advantages, and characteristics of one example may be combined in any suitable manner in one or more other examples. One skilled in the relevant art will recognize that the examples described herein may be practiced without one or more of the specific features or advantages of a particular example. In other instances, additional features and advantages may be recognized in certain examples that may not be present in all examples. Furthermore, although various examples of the aircraft 1200, the disinfecting system 100, and the method 1000 have been shown and described, modifications may occur to those skilled in the art upon reading the specification. The present application includes such modifications and is limited only by the scope of the claims.

What is claimed is:

1. An aircraft comprising:
    an interior;
    an environmental system comprising:
        at least one air supply fan configured to supply air;
        an air supply duct coupled to the at least one air supply fan and comprising a plurality of air supply outlets configured to distribute the air to the interior; and
        a plurality of air circulation fans configured to circulate the air within the interior;
    a plurality of air supply disinfectant dispensers located in the air supply duct and configured to dispense a disinfectant in the air flowing through the air supply duct and to the interior;
    a disinfectant delivery device in fluid communication with the plurality of air supply disinfectant dispensers and configured to deliver the disinfectant to the plurality of air supply disinfectant dispensers; and
    a disinfectant controller in communication with the disinfectant delivery device, the at least one air supply fan, and the plurality of air circulation fans, wherein the disinfectant controller is configured to:
        selectively initiate or selectively terminate delivery of the disinfectant from the disinfectant delivery device to any one of the plurality of air supply disinfectant dispensers; and
        selectively deactivate any one of the plurality of air circulation fans to prevent the disinfectant from entering an undesired area within the interior.

2. The aircraft of claim 1, wherein the plurality of air supply dispense the disinfectant directly into an airstream flowing through the air supply duct.

3. The aircraft of claim 1, further comprising at least one sensor configured to detect one or more conditions of the interior,
    wherein the disinfectant controller is configured to selectively control dispensation of the disinfectant from the any one of the plurality of air supply disinfectant dispenser based on the one or more conditions detected by the at least one sensor.

4. The aircraft of claim 1, further comprising a metering device located between and in fluid communication with the disinfectant delivery device and with the plurality of air supply disinfectant dispensers, wherein the metering device is configured to selectively control a quantity of the disinfectant delivered to each one of the plurality of air supply disinfectant dispenser.

5. The aircraft of claim 1, wherein:
    the disinfectant is a gas; and
    the disinfectant delivery device comprises a fan.

6. The aircraft of claim 1, wherein:
    the disinfectant is a liquid; and
    the disinfectant delivery device comprises a pump.

7. A method of disinfecting the interior of the aircraft of claim 1, the method comprising:
    circulating air through the interior of the aircraft;
    dispensing the disinfectant in the air supplied to the interior;
    determining a concentration of the disinfectant in the air within the interior; and
    upon a predetermined condition, purging the disinfectant from the interior.

8. The method of claim 7, wherein:
    circulating the air through the interior comprises:
        generating an airstream; and
        directing the airstream within the interior; and
    dispensing the disinfectant into the air comprises dispensing the disinfectant directly into the airstream.

9. The method of claim 8, wherein dispensing the disinfectant into the air further comprises dispensing the disinfectant within the interior after directing the airstream within the interior.

10. The aircraft of claim 1, further comprising an occupancy sensor in communication with the disinfectant controller and configured to generate an occupancy signal that indicates whether the interior is occupied.

11. The aircraft of claim 1, further comprising a concentration sensor in communication with the disinfectant controller and configured to generate a concentration signal that indicates a concentration of the disinfectant in the air within the interior.

12. The aircraft of claim 11, wherein the disinfectant controller is configured to determine the concentration of the disinfectant in the air within the interior based on the concentration signal.

13. The aircraft of claim 1, wherein the disinfectant controller is configured to determine a concentration of the disinfectant in the air within the interior based on an interior volume of the interior and a circulation rate of the air through the interior.

14. The aircraft of claim 1, further comprising:
    a distribution manifold in fluid communication with the disinfectant delivery device and with the plurality of air supply disinfectant dispensers,
    wherein the distribution manifold is configured to distribute the disinfectant to each one of the plurality of air supply disinfectant dispensers.

15. The aircraft of claim 1,
    wherein:
    each one of the air supply outlets has an inner diameter; and
    each one of the plurality of air supply disinfectant dispensers is located upstream from a corresponding one of the plurality of air supply outlets by a distance of at least five times the inner diameter.

16. The aircraft of claim 1, wherein:
    the interior comprises a floor; and
    further comprising at least one interior disinfectant dispenser coupled to the disinfectant delivery device and located on a floor of the interior to dispense the disinfectant directly into the air within the interior.

17. The aircraft of claim 1, further comprising:
    a disinfectant supply configured to store the disinfectant and in fluid communication with the disinfectant delivery device; and
    a disinfectant connection port located outside of the interior and in fluid communication with the disinfectant delivery device,
    wherein the disinfectant supply is located outside of the interior and is configured to be fluidly coupled with the disinfectant connection port.

18. The aircraft of claim 1, wherein the at least one disinfectant dispenser comprises a piccolo nozzle.

19. The aircraft of claim 1, further comprising a catalytic converter,
    wherein:
    the disinfectant is ozone; and
    the catalytic converter is configured to convert the disinfectant in the air within the interior to oxygen.

20. An aircraft comprising:
    an interior;
    an environmental system comprising:
        an air supply fan configured to supply air; and an air supply duct coupled to the at least one air supply fan and comprising a plurality of air supply outlets configured to distribute the air to the interior;

a plurality of air supply disinfectant dispensers positioned in the air supply duct and configured to dispense a disinfectant in the air flowing through the air supply duct and to the interior, wherein each of the plurality of air supply disinfectant dispensers is located upstream from a corresponding one of the air supply outlets by a distance of at least five times an inner diameter of the corresponding one of the air supply outlets;

a disinfectant delivery device in fluid communication with the plurality of air supply disinfectant dispensers and configured to deliver the disinfectant to the plurality of air supply disinfectant dispensers; and a disinfectant controller in communication with the disinfectant delivery device and the air supply fan, wherein the disinfectant controller is configured to selectively initiate or selectively terminate delivery of the disinfectant from the disinfectant delivery device to any one of the plurality of air supply disinfectant dispensers.

\* \* \* \* \*